(12) United States Patent
Mattey et al.

(10) Patent No.: US 9,278,141 B2
(45) Date of Patent: Mar. 8, 2016

(54) TREATMENT OF INTRACELLULAR BACTERIAL INFECTION

(71) Applicant: FIXED PHAGE LIMITED, Glasgow Strathclyde (GB)

(72) Inventors: Michael Mattey, Glasgow Strathclyde (GB); James Chadwick, Glasgow Strathclyde (GB)

(73) Assignee: Fixed Phage Limited, Glasgow Strathclyde (GB)

( * ) Notice: Subject to any disclaimer, the term of this patent is extended or adjusted under 35 U.S.C. 154(b) by 0 days.

(21) Appl. No.: 14/430,650

(22) PCT Filed: Sep. 25, 2013

(86) PCT No.: PCT/EP2013/069999
§ 371 (c)(1),
(2) Date: Mar. 24, 2015

(87) PCT Pub. No.: WO2014/049008
PCT Pub. Date: Apr. 3, 2014

(65) Prior Publication Data
US 2015/0250897 A1    Sep. 10, 2015

(30) Foreign Application Priority Data

Sep. 25, 2012  (GB) .................................. 1217097.3

(51) Int. Cl.
*A61K 47/48*    (2006.01)
*A01N 63/00*    (2006.01)
*A61K 35/76*    (2015.01)

(52) U.S. Cl.
CPC .......... *A61K 47/48853* (2013.01); *A01N 63/00* (2013.01); *A61K 35/76* (2013.01); *A61K 47/48346* (2013.01); *A61K 47/48723* (2013.01)

(58) Field of Classification Search
None
See application file for complete search history.

(56) References Cited

U.S. PATENT DOCUMENTS

| 7,482,115 B2 * | 1/2009 | Scott et al. .................. 435/5 |
| 2004/0208854 A1 | 10/2004 | Waddell et al. |
| 2009/0081173 A1 | 3/2009 | Serwer |

FOREIGN PATENT DOCUMENTS

| DE | 10 2007 036866 A1 | 2/2009 |
| WO | WO 03/000274 A2 | 1/2003 |
| WO | WO 03/093462 A2 | 11/2003 |

(Continued)

OTHER PUBLICATIONS

Katz et al. Emerging intracellular bacterial infections, Clinics in laboratory Medicine 24 (2004) 627-649, Abstract only.*
Parniske, Intracellular accomodation of microbes by plants: a common developemental program for symbiosis and disease? Current Opinion in Plant Biology 2000, 3:320-328.*

(Continued)

*Primary Examiner* — Robert A Wax
*Assistant Examiner* — Melissa Mercier
(74) *Attorney, Agent, or Firm* — Finnegan, Henderson, Farabow, Garrett & Dunner LLP

(57) ABSTRACT

An intracellular bacterial infection in a plant or animal is treated by administration to a plant cell or animal cell of a particle to which an infectious bacteriophage is covalently attached, wherein the particle is internalized by the cell. Particles with phage attached and compositions comprising the particles are provided. A formulation, for treatment of a bacterial infection, comprises bacteriophage, liquid carrier and adhesive, which dries so that the adhesive adheres the bacteriophage to a surface, one such formulation comprising liquid carrier: 85%-99.98% by weight; bacteriophage: 0.01%-5% by weight; and adhesive: 0.01%-10% by weight.

5 Claims, 4 Drawing Sheets

(56) References Cited

FOREIGN PATENT DOCUMENTS

| WO | WO 03093462 A2 * | 11/2003 |
| WO | WO 2006/047872 A1 | 5/2006 |
| WO | WO 2006047872 A1 * | 5/2006 |
| WO | WO 2006/125319 A1 | 11/2006 |
| WO | WO 2007/072049 A2 | 6/2007 |
| WO | WO 2008/109398 A1 | 9/2008 |
| WO | WO 2008109398 A1 * | 9/2008 |
| WO | WO 2012/175749 A1 | 12/2012 |

OTHER PUBLICATIONS

International Search Report for International Patent Application No. PCT/EP2013/069999 mailed Nov. 15, 2013, from the European Patent Office.

Written Opinion of the International Searching Authority for International Patent Application No. PCT/EP2013/06999 mailed Nov. 15, 2013 from the European Patent Office.

* cited by examiner

TREATMENT OF INTRACELLULAR BACTERIAL INFECTION

FIELD OF THE INVENTION

The present invention relates to bacteriophage immobilised on a particle wherein the bacteriophage retains its infectivity. In particular, the present invention relates to treatment of bacterial infections in animals and plants using those particles and to delivery of those particles for such treatments.

BACKGROUND TO THE INVENTION

In recent years, as resistance to conventional antibiotics has continued to grow and the application of chemical biocides becomes increasingly unacceptable on environmental grounds, attention has turned to alternative methods for control of bacterial infection.

One promising approach involves the application of bacteriophages, being naturally occurring ubiquitous viruses that are harmless to humans, animals, plants and fish but lethal for bacteria. Bacteriophages are specific and will infect only particular bacterial types, with several sanitation products now on the market against pathogens such as *Salmonella* and *Listeria*.

Bacteriophage immobilised on a surface retain their infectivity and are much more resistant to degradation than free bacteriophage. Immobilisation to fine particulates, such as beads, allows bacteriophages to be deployed by spray and aerosol and this mode of deployment has many applications, including treatment of human and animal bacterial disease.

Pulmonary tuberculosis is the most predominantly occurring form of tuberculosis (Tuberculosis, 2005, 85, 227-234) and the current chemotherapeutic regimen for treating pulmonary tuberculosis comprises administration of various antitubercular drugs such as isoniazid, rifampicin, ethambutol and/or pyrizinamide. Treatment is ineffective, leading to poor patient compliance and development of drug resistant strains of the intracellular bacteria that cause the disease. WO 2012/017405 provides an inhalable, microparticle based formulation. Still further therapies for this disease are, however, required.

Woiwode et al. (*Chemistry and Biology,* 2003, vol. 10, pp. 847-858) describes a phage display system that has been adapted to screen synthetic compounds. The synthetic compounds are attached to specific bacteriophage whose identity, and hence that of the synthetic compound, is encoded in the genome of the bacteriophage. A library of such bacteriophage can be screened by conventional phage display techniques and the identity of the synthetic compounds of interest can be found by identifying the specific bacteriophage it is associated with.

Rizk et al. (*Bioconjugate Chemistry,* 2012, vol. 23, pp. 42-46) describes the use of variant of substance P in receptor-mediated delivery of a 'cargo' molecule across a cell membrane. Receptor mediated delivery employs the natural endocytosis of a ligand upon binding to its receptor. Substance P is an eleven amino acid neuropeptide ligand of the neurokinin type 1 receptor and can be linked to a suitable cargo via a non-reducible thioether bond. Thus suitable cargos bearing substance P can be endocytosed upon binding of substance P to its receptor. Suitable cargos include DNA fragments, polystyrene beads and M13 bacteriophage.

US 2009/0053789 describes a method of binding bacteriophage to particles by exposing the particles to an electrical discharge in order to activate them and then mixing the activated particles with bacteriophage. In this way the bacteriophage are covalently bound to the particles.

US 2010/0285136 describes a system whereby bacteriophage are employed as a bridging molecule to bind particles comprising active agents to a substrate. This is achieved by the bacteriophage bearing both a first additional peptide that adheres to the surface of the particle and a second additional peptide that can adhere on substrate surfaces. This system may be used for delayed release of active agents. A method of screening a combinatorial phage population to find the particular bacteriophage to use is also described. WO 2008/109398 describes production of liposomes bearing modified bacteriophage for use in vaccine preparations. The vaccine antigen is displayed on a bacteriophage which is bound to the liposome.

US 2002/0001590 describes treatment of methicillin-resistant *staphylococcus aureus* (MRSA) by exposing these pathogens to bacteriophage selected from the species Myoviridae. Formulations containing these bacteriophages and their use as bactericides are also described.

Broxmeyer (*Medical Hypotheses,* 2004, vol. 62, pp. 889-893) describes the treatment an intracellular infection of macrophages using bacteriophage TM4 against virulent *Mycobacterium tuberculosis* and *Mycobacterium avium*. The bacteriophages were delivered to the pathogens as lysogens of the non-pathogenic bacterium *Mycobacterium smegmatis*.

Lunov et al. (*ACS Nano,* 2011, vol. 5, pp. 1657-1669) describe internalisation of carboxy and amino functionalised polystyrene nanoparticles by macrophages, and by differentiated and undifferentiated cells from a monocytic cell line.

The present invention relates to novel deployment of bacteriophage for treatment of bacterial infection.

An aim of the present invention is to provide compositions that are active against the growth or persistence of bacteria present within the body or cells of another organism, e.g. a plant or animal. An object of particular embodiments of the invention is to treat specific animal and plant intracellular infections.

SUMMARY OF THE INVENTION

Accordingly, the present invention provides a method of treatment or prevention of an intracellular bacterial infection in a plant or animal, comprising administration to a plant cell or animal cell of a particle to which an infectious bacteriophage is attached, wherein the particle is internalised by the cell.

In certain embodiments of the invention, an intracellular bacterial infection in an animal can be treated or prevented by administration of a particle of 1 micron or less in diameter to which an infectious bacteriophage is attached.

Embodiments of the invention may be used to treat intracellular infection in cells selected from epithelial cells, cells of the intestinal mucosa, polymorphonuclear cells, macrophages and monocytes. In specific examples described below in more detail, infection in macrophages has been treated.

In certain embodiments of the invention, an intracellular bacterial infection in a plant can be treated or prevented by administration of a particle of 5 microns or less in diameter to which an infectious bacteriophage is attached.

Also provided are a plurality of particles of mean diameter 5 microns or less, wherein infectious bacteriophage is attached thereto, for use in treating an intracellular bacterial infection in a plant, and a plurality of particles of mean diameter 1 micron or less, wherein infectious bacteriophage is attached thereto, for use in treating an intracellular infection in a plant or an animal. Still further provided are compositions comprising the particles.

It is preferred that the bacteriophage be covalently attached to the particles.

DETAILS OF THE INVENTION

A method of treatment or prevention of an intracellular bacterial infection in a plant or animal comprises administration to a plant cell or animal cell of a particle to which an infectious bacteriophage is attached, wherein the particle is internalised by the cell.

Following internalisation of the particle with phage attached, bacteria residing within the cell come into contact with and are infected and lysed by the phage, leading to phage progeny production within the bacterial cell and their subsequent release, leading in turn to further bacterial infection and lysis.

For treatment or prevention of an intracellular bacterial infection in an animal, a method of the invention may comprise administration of a particle of 1 micron or less in diameter to which an infectious bacteriophage is attached. The particles with phage attached may be 0.5 microns or less in diameter and may suitably be 10 nanometers or more in diameter. In specific examples, described below in more detail, particles of approximately 100 nm diameter were taken up by human macrophages, demonstrating effective internalisation by cells to be treated.

WO 2003/093462 describes materials that the particles may be made from. For example, particles may be made from nylon and any other polymer with amino or carboxyl surface groups, cellulose or other hydroxyl-containing polymer, polystyrene or other similar polymer, various plastics or microbeads including magnetic particles, or biological substances. More preferably, particles are made of a material commonly used in therapy/medicine; for example microbeads, which can be ingested or inhaled.

Delivery of the particles to animal cells may be via different routes. The particles may be suitably administered by inhalation, for example for infections in the lungs. The particles may be administered by injection, e.g. in formulations comprising physiologically compatible saline.

For delivery to the lungs, formulations comprising bacteriophage attached to particles in aqueous solution are sufficiently stable for delivery by nebulisation. In this regard, a number of types of known designs of nebulisers (including adaptive aerosol delivery nebulisers and dosometric nebulisers) can be used to deliver formulations of the invention. One type of high efficiency dosometric nebuliser is described in WO 2004/045689 and WO 2004/045690. Other suitable nebulisers are described in WO 2001/019437 and WO 2001/076762.

Formulations of the invention suitable for oral administration can be presented as discrete units, such as capsules, caplets or tablets. These oral formulations can also comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulations of the invention in an appropriate vehicle (vegetable oils are commonly used) to form a high viscosity mixture. This mixture is then encapsulated with a gelatin based film using technology and machinery known to those in the soft gel industry. The units so formed are then dried to a constant weight.

The invention also provides compositions and formulations comprising the particles and biologically acceptable carriers, which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

Compositions, formulations and uses of the invention are suitable for a wide range of intracellular bacteria that infect animal cells, including but not limited to *Yersinia* spp., *Neisseria gonorrhoeae*, *Shigella* spp., *Shigella flexneri*, *Listeria* spp., *Listeria monocytogenes*, *Salmonella enterica*, *Salmonella enterica* serovar *Typhimurium*, *Legionella pneumophila*, *Coxiella burnettii*, *Francisella tularensis*, *Mycobacteria* spp., *Mycobacterium tuberculosis*, *Chlamydia* spp., *Escherichia coli*, *Rickettsia* spp., *Brucella* spp., *Ehrlichia* spp. and *Burkholderia mallei*.

Within an animal host cell, bacteria can reside in two different locations. Either bacteria can be localized to a vacuole which may be derived from a phagosome formed during engulfment of the bacteria, or bacteria may colonize the host-cell cytosol. A major advantage of the intracellular location may be access to host metabolites to support bacterial multiplication in a relatively safe location and avoidance of several potent host defense mechanisms.

For instance, some bacteria such as *Yersinia* and *Neisseria gonorrhoeae* invade specific types of epithelial cells and once internalised within the host cell may remain safe from therapeutic or immune attack, enclosed in an internal vacuole bounded by host cell membrane or dispersed in the cytoplasm. Some bacteria, such as *Shigella* species, are able to multiply within host cells. *Listeria monocytogenes* is ingested with food and invades cells of the intestinal mucosa. Examples of bacteria able to multiply inside a vacuole include *Salmonella enterica* serovar *Typhimurium*, *Legionella pneumophila*, *Coxiella burnettii*, *Francisella tularensis*, *Mycobacterium tuberculosis* and obligate intracellular *Chlamydia* spp. *Listeria monocytogenes*, *Shigella flexneri*, enteroinvasive *Escherichia coli* and some *Rickettsia* species are able to enter and replicate in the cytosol of mammalian cells. Other bacteria, such as *Mycobacterium tuberculosis*, *Brucella* and *Legionella* live and grow within phagocytic cells of the immune system (polymorphonuclear cells, macrophages or monocytes) and employ various intracellular survival strategies. *Legionella pneumophila* invades pulmonary macrophages and causes pneumonia. In some cases bacteria need specific virulence factors in order to recognize, invade and multiply within eukaryotic cells, but for most the intracellular phase is useful but transient. The intracellular state may also contribute to bacterial dissemination within the host and, after evading the host defenses, they can be released into the environment or be directly transmitted to another host organism.

In examples illustrating the invention, phagocytosis by and uptake of particles of the invention bearing infectious phage has been achieved, thus demonstrating that particles of the appropriate size can be internalized and thus available for treatment of intracellular infections. Accordingly, following the invention, infections comprising bacteria located in different parts of animal cell compartments can now be treated.

For treatment or prevention of an intracellular bacterial infection in a plant, methods of the invention comprise administration of a particle of 5 microns or less in diameter to which an infectious bacteriophage is attached. The particles may be of 1 micron or less in diameter, or of 0.5 microns or less in diameter and may also be of 10 nanometers or more in diameter.

Delivery of the particles to plant cells may be via different routes. The particles may be suitably administered as an aerosol, for example by spraying onto leaves or other plant material. The particles may be administered by injection, for example directly into a plant, such as into the stem. In certain embodiments of the invention the particles are administered to the roots. This can be achieved by spraying or watering plant roots with compositions comprising the particles. In other embodiments, the particles are introduced into the xylem or phloem, for example by injection or being included in a water supply feeding the xylem or phloem.

Compositions, formulations and uses of the invention are suitable for a wide range of intracellular bacteria that infect plant cells, including but not limited to bacteria of the genera *Pseudomonas, Erwinia, Pectobacterium, Pantoea, Agrobacterium, Ralstonia, Burkholderia, Acidovorax, Xanthomonas, Clavibacter, Streptomyces, Xylella, Spiroplasma* or *Phytoplasma*, one or more or all of which can be responsible for necrotic lesions on leaves, stems and fruits, internal discolorations and decay, galls, scabs, cankers and soft rots. Trees, shrubs and herbaceous plants are all affected.

Losses from infection by the soft rot group of bacteria are especially important. They attack nearly all fruit and vegetables and can cause decay within hours. Losses of 5 to 10 percent are not uncommon. Organisms that cause soft rot live for long periods in the soil so that infection may occur before harvest. An embodiment of the invention comprises treating soil, e.g. applying a composition of the invention to soil, prior to planting. Other embodiments comprise applying a composition of the invention to soil and/or plant(s), optionally at least one or more or a plurality of times during growth of the plant(s).

Copper compounds (such as Bordeaux mixture), although primarily fungicidal, may have some effect. Antibiotics (streptomycin and/or tetracycline) may control bacteria but not cure already-diseased plants. Trees have been injected with tetracycline in the early stages of infections with some effect, but the cost and environmental concerns make antibiotics impractical. The use of biological control has been suggested; indeed the first suggestion of using bacteriophages to control plant disease was made in 1937. Bacteriophages have been found in association with buds, leaves, root nodules, roots, rotting fruit, seeds, stems and straw, crown gall tumours and in a wide range of plants. Conventionally, spraying the plant is the method employed to treat leaf and stem surfaces, however the extent of internalisation is minimal. Therefore these methods are not suitable for treating bacterial infections present beyond the accessible surface layers of a plant, or within the cells of a plant. The invention now provides for treatment of intracellular bacteria infections of plants.

Compositions are provided by the invention for treatment or prevent of bacterial infections in accordance with all aspects of the invention. Hence, the invention provides a plurality of particles of mean diameter 5 microns or less, wherein infectious bacteriophage is attached thereto, for use in treating an intracellular bacterial infection in a plant or animal. The plurality of particles may in embodiments have a mean diameter of 1 micron or less, especially for use against animal cell infections. Particle size is suitably measured using methods and apparatus recognized as standardised in the art. Examples of sizing equipment are made by Malvern Instruments, using laser diffraction methods.

In further embodiments of the invention, the plurality of particles have a mean diameter in the range 10 nm to 1 micron, suitably less than 1 micron, suitably 50 nm or greater, suitably 800 nm or less.

In specific embodiments of the invention described in greater detail below, particles of the invention have a mean diameter of approximately 100 nm.

In further preferred embodiments of the invention, substantially all of the plurality of particles have diameters less than 1 micron, more preferably 90% or more have diameters less than 1 micron, and more preferably 95% or more have diameters less than 1 micron.

Compositions are provided, comprising a plurality of these particles. The compositions may optionally also include a carrier, such as a liquid. In examples described in more detail below, compositions of the invention comprise an aqueous carrier and bacteriophages immobilized onto particles.

The carrier can also comprise an adhesive. In use a composition is applied to a plant or animal and the particles are adhered to a surface (e.g. plant surface, leaf, stem or a surface of an animal, e.g. a body part, skin, organ surface) by the adhesive. In an aqueous carrier, adhesive is dissolved in solution, or may be suspended in an aqueous carrier, and after application the composition dries, leaving a residue of adhesive that holds the particles in place. Further description of use of adhesives is set out below.

Further preferred embodiments of the invention comprise multiple bacteriophages wherein the bacteriophages are active against different strains of bacteria.

Particles for use in the invention to which bacteriophage are immobilised, preferably by covalent bonding, are generally substantially inert to the plant or animal cell to be treated. In examples, nylon particles (beads) were used. Other inert, preferably non-toxic biocompatible material may be used. In addition, the particle may be made of a biodegradable material.

It is further optional for the compositions to be adapted to increase their effectiveness. Particles can be modified to increase uptake and/or internalisation of the particle by a plant or animal cell. For example, the particle can be functionalised by the addition of carboxyl groups and/or functionalised by the addition of amino groups. One effect is that particles may enter different compartments of the target eukaryotic cell. For example carboxy- and amino-functionalized polystyrene nanoparticles of approximately 100 nm in diameter have been shown to be internalized by human macrophages and other cells by a diverse range of mechanisms.

The particles can be treated so as to have a positive surface charge, for example by immobilisation of positively charged amino acids on the particle surface.

In further embodiments of the invention, lectins which bind to bacterial toxin or enzymes which degrade the toxin, or a combination of both, can be co-immobilised with bacteriophages onto particles or onto separate particles which are delivered at the same time. Pathogenic bacteria can exert their effects by various such toxins and the destruction of bacteria, either by chemical or natural means (such as bacteriophages) can result in an increased, if transient, release of such toxins with the resulting side effects being worse than the disease, and possibly even fatal. Use of lectins in this way can reduce this effect of bacterial treatment.

Co-immobilisation of enzyme (to facilitate toxin degradation) with bacteriophage at the surface of a particle can also be used in the invention. An enzyme suitable for modifying a product of bacterial lysis can be attached to the particle.

Particles may comprise an opsonin, to improve phagocytosis. Examples include complexes containing antibodies, in particular the Fc region, antigens and the C3 component of complement, that coat the surface of bacteria. By co-immobilising bacteriophages at the surface of a particle with opsonin-like components (e.g. combinations of antigen, antibody and C3 component of complement, or peptide or other fractions of each), in combination or individually, phagocytosis of the particle is promoted.

Iron is an essential nutrient for the growth and metabolism of nearly all bacteria and an essential co-factor of numerous metabolic processes. In animal infection availability of iron is limited because iron is sequestered by the high affinity binding proteins lactoferrin (mucosal surfaces) and transferrin (serum). *M. tuberculosis* phagosomes contain additional transferrin receptors and upregulation may occur at membranes of other cell compartments containing intracellular pathogens. In embodiments of the invention, the bacteriophage attached to the particle or the particle itself expresses or comprises transferrin or lactotransferrin. Such phage or particles may be may be preferentially phagocytosed by animal cells infected with intracellular bacteria and/or subsumed within intracellular compartments containing bacteria. In specific embodiments of the invention, a bacteriophage is co-immobilised onto a particle with transferrin or lactoferrin.

Additionally adhesion to a surface is enhanced in further embodiments of the invention in one or more of a number of ways.
- The dispersing solution can be so composed that it provides an adhesive function just sufficient to retain particles at the desired site without interfering with the antibacterial action of immobilised bacteriophage. This can be brought about by, say, the addition of starch or other material.
- The carrier particles can be charged to provide and promote attachment to a surface perhaps having an opposite charge. This can equally also apply to particles dispensed as powders or within solution.
- The carrier particles may have a ligand attached that promotes attachment to a particular surface.

Thus, in a related invention, optionally for use in combination with other inventions and embodiments described elsewhere herein, there are provided formulations with enhanced adhesion of bacteriophage to surfaces to which the bacteriophage is applied. Hence, the related invention provides adhering formulations, for treatment of a bacterial infection, comprising bacteriophage, liquid carrier and adhesive. In use, the formulations dry so that the adhesive adheres the bacteriophage to a surface.

In such formulations, the carrier is suitably an aqueous carrier, and preferably comprises or is water.

A typical formulation is composed mainly of the liquid carrier. The proportions of the components will vary. In embodiments, the formulations comprises
    liquid carrier: 85%-99.98% by weight;
    bacteriophage: 0.01%-5% by weight; and
    adhesive: 0.01%-10% by weight.

The liquid carrier by weight is preferably 90% or more by weight; the bacteriophage component (preferably in the form of particles with bacteriophage attached as described elsewhere herein) preferably makes up 0.1%-4% by weight; and the adhesive 0.1%-10% by weight, more preferably 1% by weight to 5% by weight.

In use of formulations of the invention, bacteriophage-containing compositions are applied by aerosol, and hence preferred formulations are sprayable.

A method of treatment or prevention of bacterial infection comprises applying an adhering formulation of the invention to a surface and allowing the formulation to dry. Enhanced fixing of the bacteriophage, e.g. particles bearing the bacteriophage, is achieved, giving resistance to loss of the bacteriophage and improved anti-bacterial activity in situ.

Particularly suitable adhesives are water-soluble, and examples of adhesives for use in the invention include animal protein based adhesive, plant-based glue, solvent-type glue, synthetic monomer glue, sugar, complex sugar, starch and a mixture of any of these. Specifically, the adhesive may consist of or comprise bone glue, fish glue, hide glue, hoof glue, rabbit skin glue, albumin glue, casein glue, meat glue, canada balsam (natural resin), coccoina, gum arabic (natural resin), postage stamp gum, latex (natural rubber), library paste (a starch-based glue), methyl cellulose, mucilage, resorcinol resin, starch, urea-formaldehyde resin, polystyrene cement/butanone, acrylonitrile, cyanoacrylate ("superglue", "krazy glue"), acrylic resorcinol glue, epoxy resin, epoxy putty, ethylene-vinyl acetate (a hot-melt glue), phenol formaldehyde resin, polyamide, polyester resin, polyethylene (a hot-melt glue), polypropylene, polysulfide, polyurethane, polyvinyl acetate, polyvinyl alcohol (PVA), polyvinyl chloride (PVC), polyvinyl chloride emulsion, polyvinylpyrrolidone, rubber cement, silicones, styrene acrylic copolymer.

Examples of specific adhesive-containing embodiments of the invention are the following formulations:
Formulation A
    water: 92% by weight;
    bacteriophage 3% by weight
    (covalently attached to particles of mean diameter 100 nm)
    PVA 5% by weight.
Formulation B
    water: 94% by weight;
    bacteriophage 2% by weight
    (covalently attached to particles of mean diameter 100 nm)
    starch 4% by weight.

Bacteriophage for use in these adhering formulations are preferably attached to substrates such as particles, for example as described in WO 2003/093462 and WO 2007/072049. The bacteriophage are preferably also as described herein for treatment of intracellular infections in plants and animals.

The following optional and preferred features apply in relation to all inventions and embodiments thereof.

Immobilisation or attachment of bacteriophage to the particle substrate may be achieved in a number of ways. Preferably, bacteriophage are immobilised via bonds, more preferably covalent bonds formed e.g. between the bacteriophage coat protein and the substrate.

Further, bacteriophage are preferably immobilised to the substrate via their head groups or nucleocapsid by activating the substrate before the addition and coupling of bacteriophage.

The term "activated/activating/activation" is understood to mean the activation of a substrate by reacting said substrate with various chemical groups (leaving a surface chemistry able to bind viruses, such as bacteriophage head or capsid groups).

Activation of said substrate may be achieved by, for example, preliminary hydrolysis with an acid, preferably HCl followed by a wash step of water and an alkali to remove the acid. Preferably, said alkali is sodium bicarbonate. Binding of bacteriophage via their head groups is advantageous. In the case of complex bacteriophage for example, binding via head groups leaves the tail groups, which are necessary for bacteria-specific recognition, free to infect, i.e., bind and penetrate a host bacterial cell. A plurality of various strain-specific bacteriophage, may be immobilised to a substrate at any one time.

Coupling of phage to a substrate is as a result of the formation of covalent bonds between the viral coat protein and the substrate such as through an amino group on a peptide, for example a peptide bond. "Coupling Agents" that aid this process vary, and are dependent on the substrate used. For example, for coupling to the substrate nylon or other polymer with amino or carboxy surface groups the coupling agents carbodiimide or glutaraldehyde may be used.

Further details of methods and preferred methods for attachment of bacteriophage to particles are described in more detail in WO 2003/093462 and WO 2007/072049, the contents of which are incorporated by reference.

The invention is suitable for use with bacteriophage in general, without limitation to the bacteriophage strain, though preferably with lytic bacteriophage.

Bacteriophage for the invention include bacteriophage in general without limitation provided that the bacteriophage is obtainable and its host or target bacteria can be cultured and infected in culture. The bacteriophage can be ssRNA, dsRNA, ssDNA or dsDNA bacteriophage, with either circular or linear arrangement of the genetic material, and which infect cells of bacteria. The suitable bacteriophage include Myoviridae, Siphoviridae, Podoviridae, Lipothrixviridea, Rudiviridae, Ampullaviridae, Bacilloviridae, Bicaudaviridae, Clavaviridae, Corticoviridae, Cystoviridae, Fusseloviridae, Globuloviridae, Guttavirus, Inoviridae, Leviviridae, Microviridae, Plasmaviridae and Tectiviridae.

The invention is now illustrated in specific embodiments with reference to the accompanying drawings in which.

EXAMPLE 1

Uptake of Submicron Polymeric Particles, with Bacteriophage Attached, into Macrophages Experimental Nylon particles (100 nm mean diameter) containing immobilised bacteriophages (phage Shield, host bacteria *Salmonella typhimurium*) were incubated with CD14$^+$ macrophages. The macrophages were visualised using light microscopy to determine the presence of beads and then washed and plated onto a lawn of host bacteria. Any surviving active immobilised bacteriophages produce a "plaque" which highlights inhibition of bacterial growth.

Cell Culture:

CD14$^+$ cells (macrophage) isolated from human blood samples were cultured in suspension in Dulbecco's Modified Eagle's Medium (DMEM) supplemented with 2 mM L-glutamine and 10% fetal bovine serum with a 5% $CO_2$ atmosphere at 37° C. A split ratio of 1:5 was used, the medium being replaced every 2 to 3 days.

Particle Production:

Nylon particles were treated by corona discharge (75 kV field) and rapidly added to a bacteriophage suspension at $1\times10^9$ pfu/ml. Particles were washed 3 times to remove non-bound bacteriophages.

Incubation:

Macrophages were seeded in tissue culture microscopy chambers at a concentration of $5\times10^5$ cells cm$^{-2}$ and cultured for 72 h at 37° C. Corona treated beads were added at a concentration of $1\times10^9$ beads/ml and the cells were incubated at 37° C. for 60 min. Cells were also inoculated with untreated $1\times10^9$ beads and with no beads as a negative control.

Visualisation of Macrophages:

Macrophages were visualised using light microscopy at 20× and 40× magnification. Images of cells were taken using Cell-D microscopy software and the bead structures were measured using the software measurement grid to confirm the presence of beads inside the cell.

Figure 1:
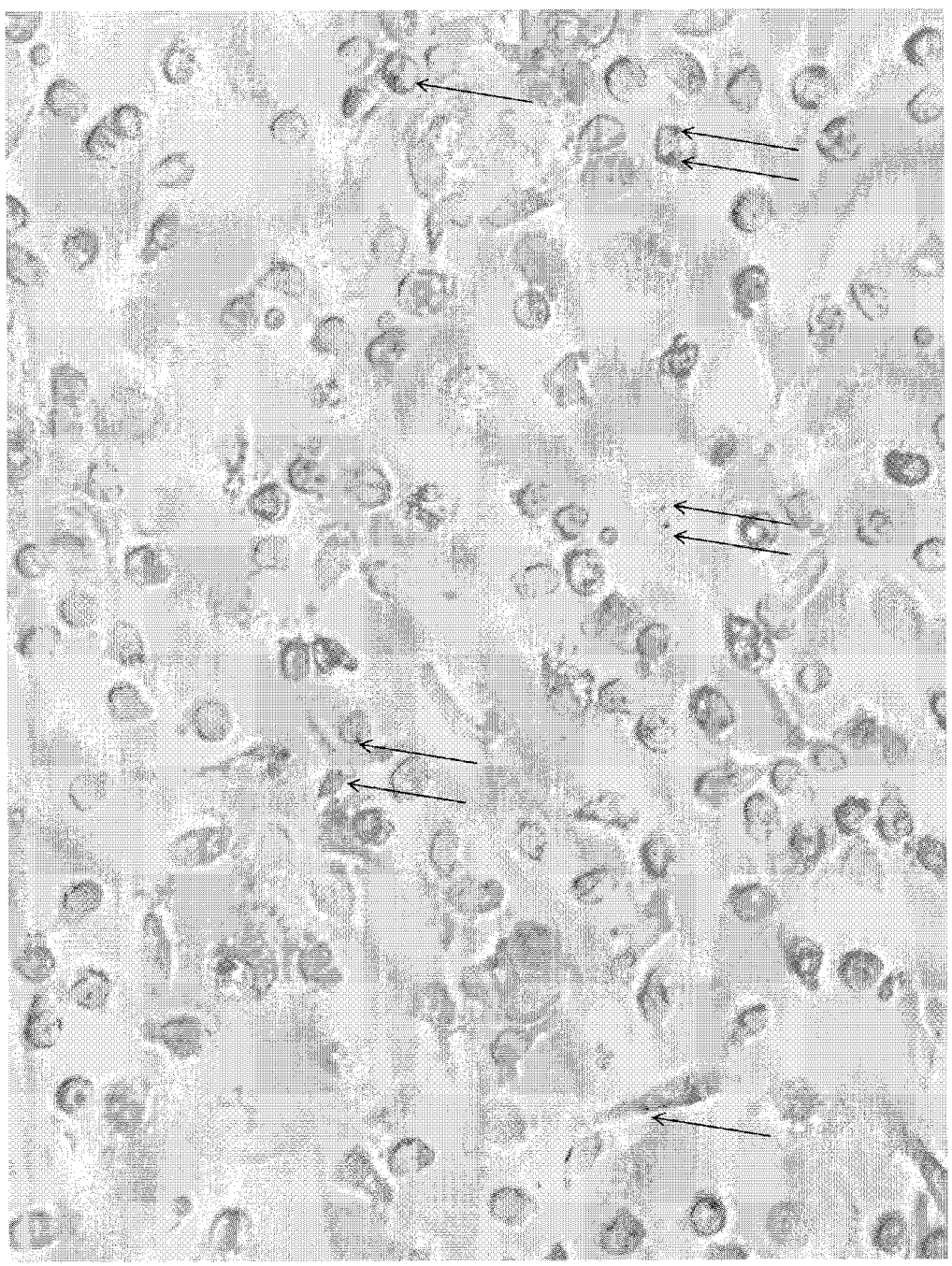
FIG. 1 shows a ×20 magnification micrograph of macrophages incubated with nylon beads carrying immobilised bacteriophages.
Figure 2:
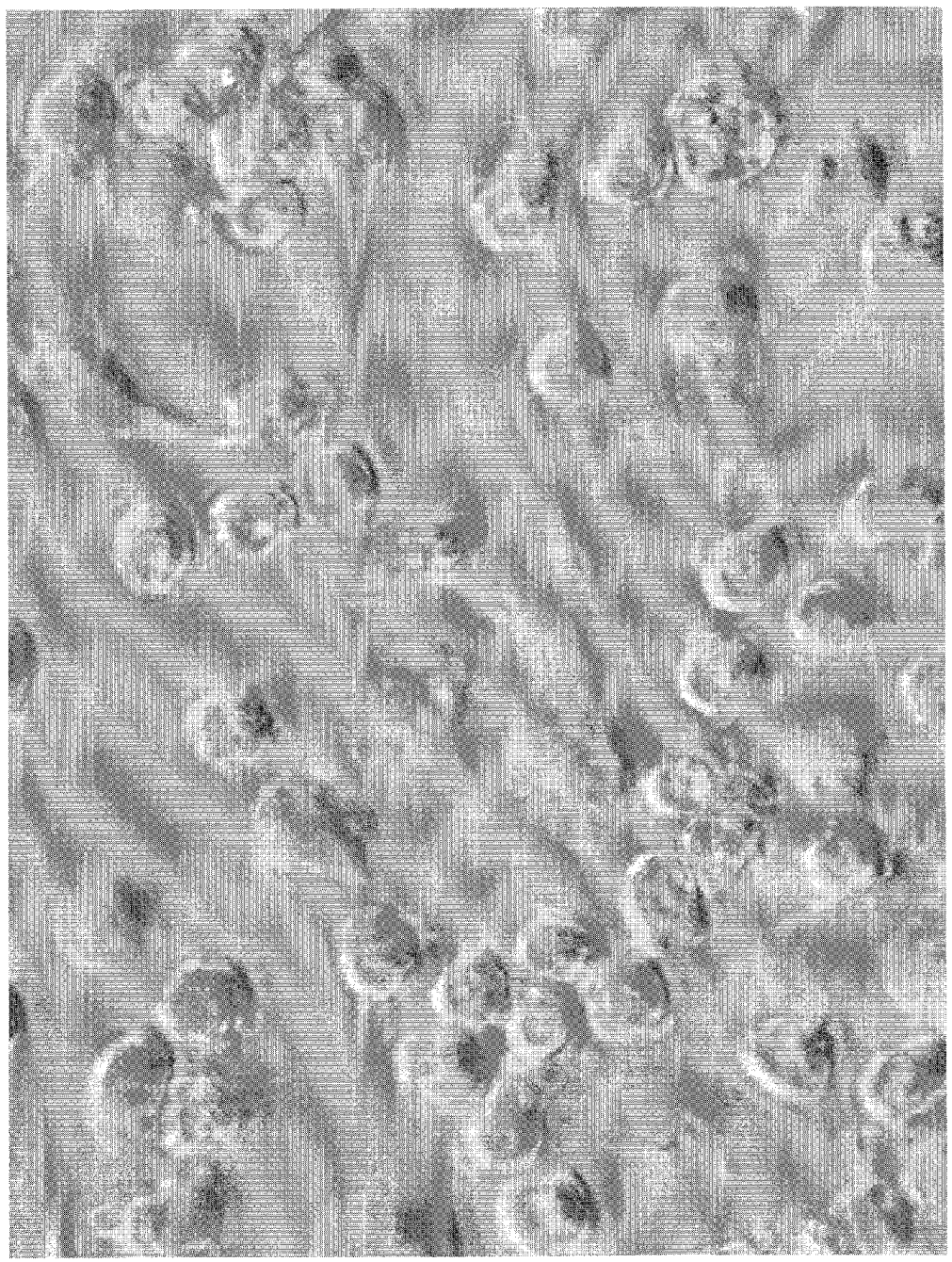
FIG. 2 shows a ×20 magnification micrograph of the result of a negative-control sample of the experiment shown in FIG. 1.

Results:

FIG. 1 shows a ×20 magnification micrograph of macrophages incubated with nylon beads carrying immobilised bacteriophages. The macrophages were prepared by the method set out above and have internalised the beads. Arrows indicate the phagocytosed particles. In FIG. 2 there is a ×20 magnification micrograph of the result of the negative-control sample of the experiment shown in FIG. 1. In this case the macrophages were incubated in the absence of the nylon beads carrying immobilised bacteriophages. In contrast to the result shown in FIG. 1, there is no evidence of phagocytosed particles.

Figure 3:
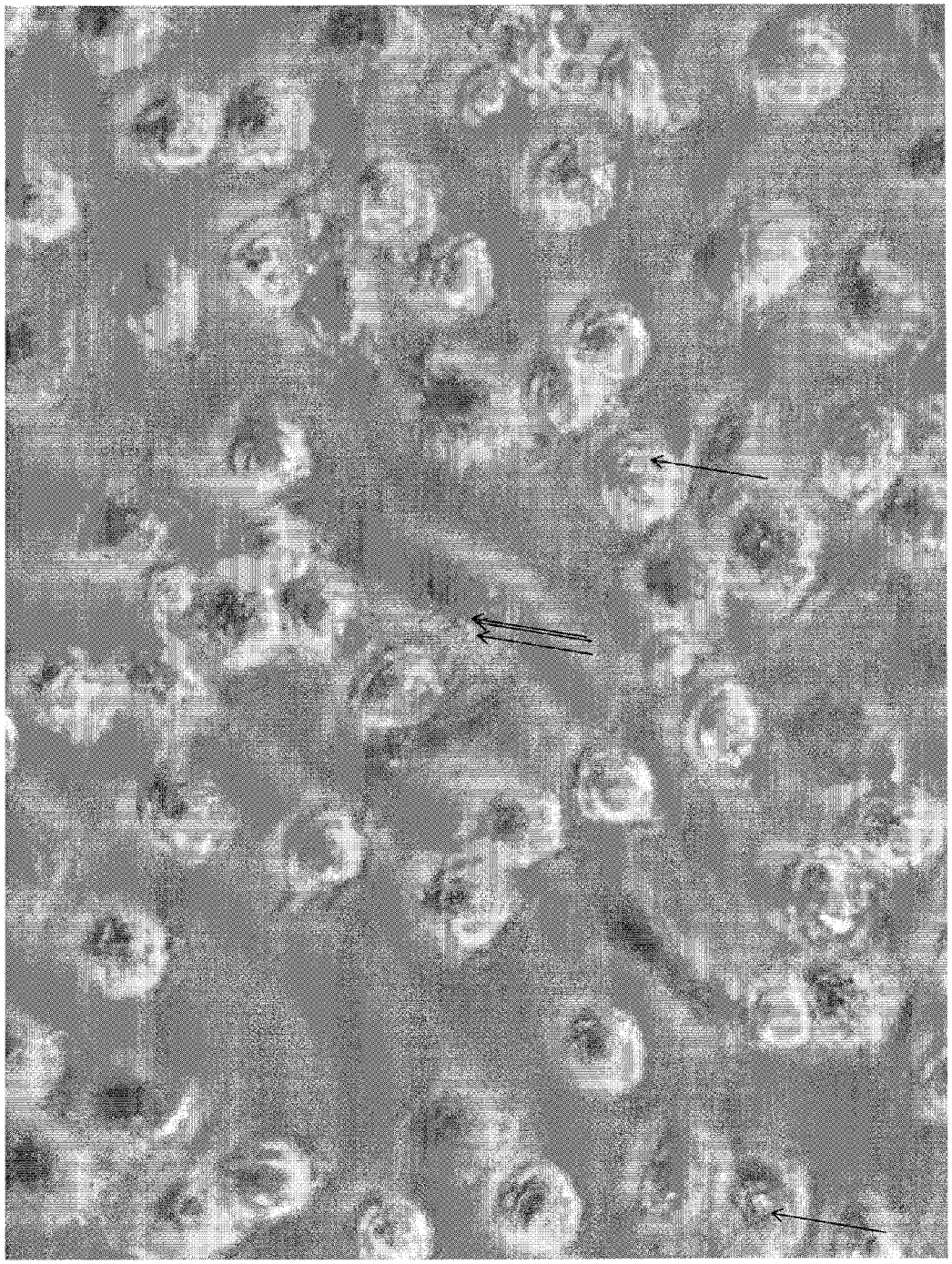
FIG. 3 shows a ×40 magnification micrograph of macrophages incubated with nylon beads carrying immobilised bacteriophages.
Figure 4:
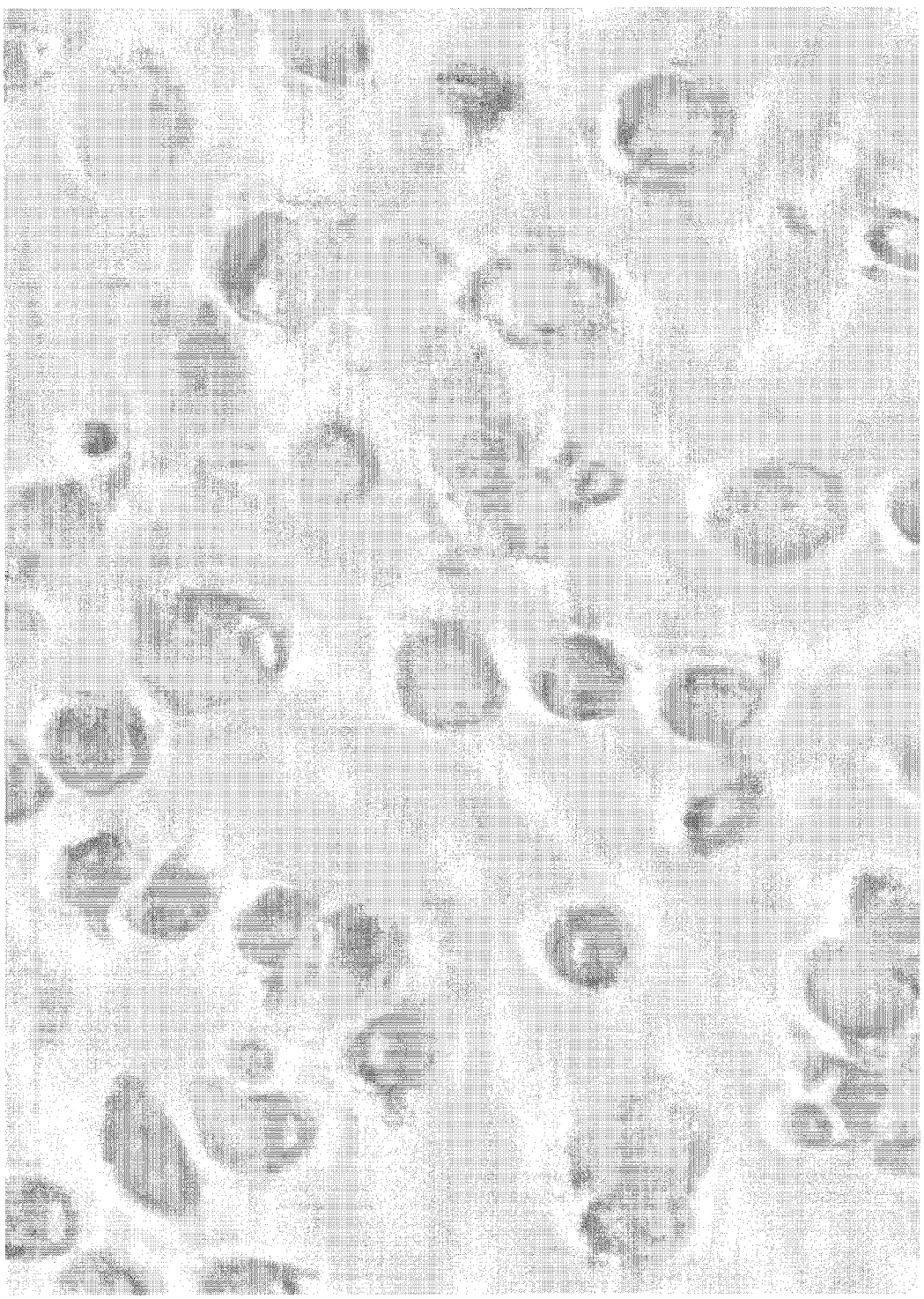
FIG. 4 shows a ×40 magnification micrograph of the result of a negative-control sample of the experiment shown in FIG. 3.

FIG. 3 shows a ×40 magnification micrograph of macrophages incubated with nylon beads carrying immobilised bacteriophages. The macrophages were prepared by the method set out above and have internalised the beads. Arrows indicate the phagocytosed particles. In FIG. 4 there is shown a ×40 magnification micrograph of the result of the negative-control sample of the experiment shown in FIG. 3. In this case the macrophages were incubated in the absence of the nylon beads carrying immobilised bacteriophages. In contrast to the result shown in FIG. 3, there is no evidence of phagocytosed particles.

EXAMPLE 2

Testing the Effect of Immobilised Bacteriophage on the Invasive *Salmonella enterica* Subsp *Typhimurium* Strain SL1344 in Macrophages Testing was carried out as follows:

Method

Raw 264 macrophage cells (http://www.lgcstandards-atcc.org/products/all/TIB-71.aspx?geo_country=gb) were seeded at $5\times10^4$ cells/ml in a 24-well tissue culture plate in RPMI (RPMI-1640, Roswell Park Memorial Institute) medium containing glutamine and 10% fetal calf serum (FCS) and incubated overnight at 37° C., 5% $CO_2$.

The macrophage monolayers were activated overnight with 1 μg/ml lipopolysaccharide (LPS) which was added to the media and incubated overnight at 37° C., 5% $CO_2$. LPS-activated macrophages show a more consistent level of invasion by the *Salmonella* bacteria.

Macrophage monolayers were washed and new medium added without antibiotics. Various test combinations of immobilised bacteriophage and bacteria were added as detailed in the table 1, below.

TABLE 1

Test conditions.

| Combinations | Time (hr) |
| --- | --- |
| SL1344 alone | 1 hr |
| SL1344 + bacteriophage | 1 hr |
| SL1344 alone | 2 hr |
| SL1344 + bacteriophage | 2 hr |
| SL1344 then bacteriophage | 1 hr bacteria followed by another 1 hr with bacteriophage |

100 µl of bacteria with or without bacteriophage were added to the macrophages. After the desired incubation time the medium was removed and the macrophages washed twice with 1 ml of phosphate-buffered saline (PBS). 1 ml of RPMI with gentamycin (100 µg/ml) was added and the cells incubated for a further 1 hr (37° C., 5% $CO_2$). The medium was then removed and the monolayers washed twice with 1 ml PBS. The macrophages were then lysed with 200 µl of 2% Triton X-100.

Samples were plated onto brain heart infusion (BHI) and BHI overlays containing SL1344 to enumerate the numbers of SL1344 and bacteriophages, respectively, that were internalised by the macrophages.

20 µl of sample dilutions were inoculated onto plates to deduce the numbers of bacteria which were added onto the macrophage monolayers. The numbers of bacteriophage were estimated by adding 100 µl of bacteriophage sample to 100 µl of overnight SL1344 culture in a 5 ml agar overlay.

SL1344 was added to each well at $3.5 \times 10^5$ colony forming units per well.

Beads bearing immobilised bacteriophage—an estimated $1 \times 10^{13}$ beads/ml were diluted 1:100 and 100 µl added to each well. Thus it is estimated that $1 \times 10^{10}$ beads/ml were added to each well. The number of SL1344 invading the macrophages was then calculated.

Initial results showed in some cases elimination of infectious bacteria and in others a reduction in the infectious load of bacteria in the macrophages. Further testing to quantify the results is ongoing.

The invention thus provides a method of treatment or prevention of an intracellular bacterial infection in a plant or animal and compositions suitable therefor.

REFERENCES

1. Corsaro, D., D. Venditti, M. Padula, and M. Valassina. 1999. *Intracellular life. Crit. Rev. Microbiol.* 25:39-79.
2. von Dohlen, C. D., S. Köhler, S. T. Alsop, and W. R. McManus. 2001. *Mealybug beta-proteobacterial endosymbionts contain gamma-proteobacterial symbionts. Nature* 412:433-436.
3. Rendulic, S., P. Jagtap, A. Rosinus, M. Eppinger, C. Baar, C. Lanz, H. Keller, C. Lambert, K. J. Evans, A. Goesmann, F. Meyer, R. E. Sockett, and S. C. Schuster. 2004. *A predator unmasked: life cycle of Bdellovibrio bacteriovorus from a genomic perspective. Science* 303:689-692.
4. Guerrero, R., C. Pedros-Allo, I. Esteve, J. Mas, D. Chase, and L. Margulis. 1986. *Predatory prokaryotes: predation and primary consumption evolved in bacteria. Proc. Natl. Acad. Sci. USA* 83:2138-4212.
5. Martin, M. O. 2002. *Predatory prokaryotes: an emerging research opportunity. J. Mol. Microbiol. Biotechnol.* 4:467-477.
6. Goebel, W., and R. Gross. 2001. *Intracellular survival strategies of mutualistic and parasitic prokaryotes. Trends Microbiol.* 9:267-273
7. Ochman, H., and N. A. Moran. 2001. *Genes lost and genes found: evolution of bacterial pathogenesis and symbiosis. Science* 292:1096-1099.
8. Finlay, B. B., and S. Falkow. 1997. *Common themes in microbial pathogenicity revisited. Microbiol. Mol. Biol. Rev.* 61:136-169.
9. Gross, R., J. Hacker, and W. Goebel. 2003. *The Leopoldina international symposium on parasitism, commensalism and symbiosis—common themes, different outcome. Mol. Microbiol.* 47:1749-1758.
10. Oleg Lunov, Tatiana Syrovets, Cornelia Loos, Johanna Beil, Michael Delacher, Kyrylo Tron, G. Ulrich Nienhaus, Anna Musyanovych, Volker Mailänder, Katharina Landfester, and Thomas Simmet *Differential Uptake of Functionalized Polystyrene Nanoparticles by Human Macrophages and a Monocytic Cell Line ACS Nano,* 2011, 5 (3), pp 1657-1669

The invention claimed is:

1. A composition comprising a plurality of particles of mean diameter 1 microns or less, wherein an infectious bacteriophage is covalently attached thereto, for use in treating an intracellular bacterial infection in a plant or animal, wherein the particles are functionalised by the addition of amino groups.

2. A composition comprising a plurality of particles of mean diameter 1 microns or less, wherein an infectious bacteriophage is covalently attached thereto, for use in treating an intracellular bacterial infection in a plant or animal, wherein an antibody is attached to the particles.

3. A composition comprising a plurality of particles of mean diameter 1 microns or less, wherein an infectious bacteriophage is covalently attached thereto, for use in treating an intracellular bacterial infection in a plant or animal, wherein an opsin is attached to the particles.

4. A composition comprising a plurality of particles of mean diameter 1 microns or less, wherein an infectious bacteriophage is covalently attached thereto, for use in treating an intracellular bacterial infection in a plant or animal, wherein transferrin or lactoferrin is attached to the particles.

5. A composition comprising a plurality of particles of mean diameter 1 microns or less, wherein an infectious bacteriophage is covalently attached thereto, for use in treating an intracellular bacterial infection in a plant or animal, wherein a lectin is attached to the particles.

* * * * *